US006365800B1

(12) United States Patent
Caimi

(10) Patent No.: US 6,365,800 B1
(45) Date of Patent: Apr. 2, 2002

(54) TRANSGENIC CROPS ACCUMULATING FRUCTOSE POLYMERS AND METHODS FOR THEIR PRODUCTION

(75) Inventor: Perry G. Caimi, Kennett Square, PA (US)

(73) Assignee: E. I. du Pont Nemours & Company, Wilmington, DE (US)

( * ) Notice: Subject to any disclaimer, the term of this patent is extended or adjusted under 35 U.S.C. 154(b) by 0 days.

(21) Appl. No.: 09/245,323

(22) Filed: Feb. 5, 1999

Related U.S. Application Data

(60) Provisional application No. 60/077,727, filed on Mar. 12, 1998.

(51) Int. Cl.[7] ........................ C12N 15/29; C12N 15/54; C12N 15/82; C12P 19/04; A01H 5/00

(52) U.S. Cl. ........................ 800/284; 800/287; 800/320; 800/320.1; 536/23.6; 435/101; 435/193; 435/419

(58) Field of Search ................................ 800/284, 287, 800/320.1, 320; 536/23.6; 435/419, 193, 101

(56) References Cited

U.S. PATENT DOCUMENTS 5,986,173 A 11/1999 Smeekens et al. .......... 800/284

FOREIGN PATENT DOCUMENTS

| | | | |
|---|---|---|---|
| WO | 94/04692 | | 3/1994 |
| WO | 94/14970 | | 7/1994 |
| WO | 95/13389 | A | 5/1995 |
| WO | WO 96/01904 | | 1/1996 |
| WO | WO 96/21023 | | 7/1996 |

OTHER PUBLICATIONS

Vijn et al. Plant Journal 11(3):387–398, 1997.*

Smeekens et al. Biochem. Soc. Trans. 19:565–569, 1991.*

Turk et al. New Phytol. 136(1):29–38, 1997.*

(Takao Uchiyama) M. Suzuki & N. Chatterton, eds. CRC Press Inc., Boca Raton, FL, pp. 169–190, (1993) Chapter 5.

Fuchs, A., (1993), Science and Technology of Fructans, M. Suzuki and N. Chatterton, eds. CRC Press Inc., Boca Raton, FL., pp. 319–352.

Sevenier et al., (1998), Nature Biotechnology, vol. 16:843–846.

Ebskamp et al., (1994), Biotechnology, vol. 12:272–275.

Oparka, W. and Wright, K., (1988), Planta, vol. 174:123—126.

Caimi et al., (1996), Plant Physiol., vol. 110:355–363.

Koops, A. and Jonker, H. (1994), J. Exp. Bot. 45:1623–1631.

Chambert, R., and Petit–Glatron, M. (1991) Biochem.J. 279:35–41.

Edelman, J. and Jefford, T., (1968), New Phytol., vol. 67:517–531.

Vijn et al., (1997), The Plant Journal, 11:387–398.

* cited by examiner

*Primary Examiner*—David T. Fox

(57) ABSTRACT

A method for producing fructose polymers of various lengths through expression of plant-derived FTF genes in transgenic monocot plants is disclosed. Also disclosed are transgenic monocot plants seeds derived from said plants wherein the level of fructan that accumulates in the cells of the transgenic monocot plants and seeds is increased when compared to the level of fructan that accumulates in the cells of monocot plants and that do not contain the instant chimeric gene(s) encoding plant-derived FTF genes.

19 Claims, 5 Drawing Sheets

TRANSGENIC CROPS ACCUMULATING FRUCTOSE POLYMERS AND METHODS FOR THEIR PRODUCTION

This application claims the benefit of U.S. Provisional Application No. 60/077,727, filed Mar. 12, 1998.

FIELD OF THE INVENTION

The present invention concerns methods for synthesis and accumulation of fructose polymers in transgenic maize (*Zea mays* L.) by selective expression of plant-derived fructosyltransferase genes.

TECHNICAL BACKGROUND

Higher plants accumulate various commercially useful carbohydrate polymers such as cellulose, starch and fructan. Starch and cellulose are currently used in numerous food and non-food applications in their native form, but are more likely to be enzymatically or chemically modified, which greatly expands their usefulness.

Fructans are linear or branched polymers of repeating fructose residues. The number of residues contained in an individual polymer, also known as the degree of polymerization (DP), varies greatly depending on the source from which it is isolated. For example, fructan synthesized by fungal species, such as in *Aspergillus syndowi* may contain only two or three fructose residues. By contrast, polymers with a DP of 5000 or greater are synthesized by several bacterial lines, including *Bacillus amyloliquefaciens* and *Streptococcus mutans*. Intermediate sized fructan, with a DP of 3 to 60, are found in over 40,000 plant species (*Science and Technology of Fructans*, (1993) M. Suzuki and N. Chatterton, eds. CRC Press Inc., Boca Raton, Fla., pp. 169–190).

Regardless of size, fructose polymers are not metabolized by humans. Because of this, and due to their relative sweetness, small fructans with a DP of 3–4 are used in a wide variety of low calorie food products. Polymer size is critical to its commercial use. High DP polymers are not sweet, however, they do provide texture to food products very similar to that of fat. High DP fructan used as a fat replacer also contributes very little to the caloric value of the product.

Fructans are also considered to be an excellent source of fructose for the production of high fructose syrup (Fuchs, A. (1993) in *Science and Technology of Fructans*, M. Suzuki and N. Chatterton, eds. CRC Press Inc., Boca Raton, Fla., pp. 319–352). Simple hydrolysis of fructan into individual fructose residues has a tremendous advantage over the current, technically demanding process of enzymatically converting starch into high fructose syrup. Using fructan as the starting material would, therefore, significantly reduce production costs.

The commercial potential for fructan is extremely high, however, its use is severely limited due mainly to the high cost of production. Fructan used in low-calorie foods is currently produced by fermentation culture. Larger polymers synthesized by bacteria are not currently produced on a commercial scale. Isolation from plants would reduce the production costs, but fructan is not found in many crops of agricultural importance. Traditional crops, adapted to wide growing regions, such as oat, wheat and barley accumulate fructan, but only at extremely low levels. Fructan is currently harvested from plants on a relatively small commercial scale and only from a single plant species, *Cichorium intybus*.

Transgenic crops accumulating fructan through expression of chimeric fructosyltransferase (FTF) genes would have a significant advantage over native fructan-storing plants by making use of established breeding programs, pest resistance and adaptation to a variety of growing regions throughout the world. Examples of fructan synthesis in transgenic plants containing genes from bacterial species, such as Bacillus, Streptococcus and Erwinia have been reported (Caimi et al., (1996) *Plant Physiol.* 110:355–363; Ebskamp et al., (1994) *Biotechnol.* 12:272–275; Rober et al., (1996) *Planta* 199:528–536). Synthesis of fructan in these non-fructan-storing plants was demonstrated, but accumulation was often very low and in tissues where high levels of fructan were reported to have a detrimental effect on plant development.

Several important differences between transgenic plants expressing chimeric bacterial FTF genes and native fructan-storing plants were reported. The most obvious difference was in the size of the polymers synthesized. Transgenic lines containing bacterial FTF genes accumulate fructan with a DP of greater than 5000 (Ebskamp et al., (1994) *Biotechnol.* 12:272–275; Caimi et al., (1996) *Plant Physiol.* 110:355–363). Polymers synthesized in transgenic plants are, therefore, several thousand times larger than fructans which accumulate in plants such as chicory (*Cichorium intibus* L.) and Jerusalem artichoke (*Helinathus tuberosus* L.).

Differences in the specificity for donor and acceptor molecules have also been reported for bacterial and plant FTFs. The bacterial enzymes are known to release significant amounts of fructose to water as an acceptor (invertase activity), whereas the plant enzymes do not have invertase activity (Chambert, R. and Petit-Glatron, M. (1993) in *Inulin and Inulin Containing Crops*, A. Fuchs ed. Elsevier Press, Amsterdam. pp. 259–266). Fructose, liberated from sucrose by invertase activity, can not be used to increase the length of a polymer. Bacterial FTFs, therefore, convert sucrose to fructan less efficiently than do the plant enzymes.

The two classes of FTFs also differ in their affinity for sucrose, the sole substrate. Jerusalem artichoke sucrose-sucrose-fructosyltransferase (SST) has a Km for sucrose reported to be approximately 100 mM (Koops, A. and Jonker, H., (1994) *J. Exp. Bot.* 45:1623–1631). By contrast, the bacterial enzyme has a much lower Km of approximately 20 mM (Chambert, R., and Petit-Glatron, M. (1991) *Biochem. J.* 279:35–41). This difference may have a critical effect on fructan synthesis, resulting in higher or lower levels of accumulation, depending on the concentration of sucrose in the cell. The fundamental differences between FTF enzymes prevents meaningful predictions regarding the outcome of expression of plant genes in transgenic tissue, based on expression of bacterial FTF genes.

Predicting whether or not fructan would accumulate in a transgenic line containing the plant-derived FTF genes could be significantly enhanced if a greater understanding of the fructan metabolic pathway in native fructan-storing plants existed. The currently accepted model for fructan synthesis in plants suggests that synthesis is a two step reaction. The initial reaction involves the enzyme sucrose-sucrose-fructosyltransferase (SST). SST catalyzes the synthesis of a trisaccharide from two sucrose residues. The second step, chain elongation, is carried out by the enzyme fructan-fructan-fructosyltransferase (FFT), (Edelman J., and Jefford T. (1968) *New Phytol.* 67:517–531. The model has been applied to all fructan-storing plants (ca 45000 species). However, it is based largely on data from a single species, *Helianthus tuberosus*, and has undergone several revisions.

A recent study demonstrates that the SST can act alone in producing long chain fructan (Van der Ende, W. and Van Laere, A., (1996) *J. Exp. Bot.* 47:1797–1803). Thus, additional revisions in the model are necessary and suggests that there is only a rudimentary knowledge of fructan synthesis in plants.

Examples of fructan synthesis in transgenic plants containing microbial or plant-derived FTF genes has been reported (Vijn, et al., (1997) *The Plant J.* 11:387–398; Smeekens et al., WO 96/01904; Van Tunen et al., WO 96/21023; Sevenier et al., (1998) *Nature Biotechnology* 16:843–846). This previous work involves expression of microbial or plant-derived SST genes only in transgenic dicotyledenous (dicots) plants. The present invention describes a method of increasing the level of fructan synthesis in transgenic monocotyledonous plants containing plant-derived SST genes or plant-derived SST and FFT genes.

Numerous differences between monocotyledonous (moncots) plants and dicots exist which inhibit useful extrapolation of events occurring in one plant based on data from another. These differences include, but are not limited to, the competition for sucrose as an energy source among biosynthetic pathways in various plant organs and among biosynthetic pathways in different plant species.

Dicots and monocots are known to differ significantly in the transport and metabolism of carbohydrate. For example, pea (*Pisum sativum* L.), a dicot, transports glucose-6-phosphate into amyloplasts, the site where starch synthesized and stored. In monocots, such as maize, ADPglucose is transported into the amyloplast (Denyer et al., (1996) *Plant Phys.* 112:779–785). This seemingly simple difference illustrates a profound difference in the metabolic pathways necessary for processing the various forms of carbohydrate transported into the amyloplast in the two separate plants.

Transport of sucrose in plants also differs among plant species. Specialized cells (basal endosperm transfer cells or BET cells) are adapted for the transport and metabolism of sucrose in maize kernels. The majority (greater than 90%) of sucrose transported to maize seeds is believed to be hydrolyzed in the specialized BET layer (Shannon, J. (1972) *Plant Physiol.* 49:198–202). The resulting hexose sugars are transported to the developing endosperm cells and resynthesized as sucrose prior to entering the starch biosynthetic pathway. In contrast to maize, sucrose is directly transported to tubers of potato plants and enters the starch pathway unhydrolyzed (Oparka, K. and Wright, K. (1988) *Planta* 174:123–126).

Although poorly understood, exploiting the differences between monocots and dicots could not be considered a new concept. These differences are what drives the commercialization of herbicides such as 2,4-D which is tremendously toxic to dicots, but has no effect on monocot species. In this light, it seems clear that recent examples of transgenic dicot species containing a plant derived FTF gene (Vijn, et al., (1997) *The Plant J.* 11:387–398; Smeekens et al., WO 96/01904; Van Tunen et al., WO 96/21023; Sevenier et al., (1998) *Nature Biotechnology* 16:843–846) can have no bearing on predicting the successful expression of FTF genes in moncot species. Variations in carbohydrate concentration, transport and metabolism among plant species, especially between moncots and dicots, are clearly too great to allow generalization.

SUMMARY OF THE INVENTION

This invention discloses a method for producing fructose polymers of various lengths through expression of plant-derived FTF genes in a transgenic monocot species. More specifically, the invention describes a chimeric gene comprising a tissue specific promoter, operably linked to the coding sequence for a sucrose-sucrose-fructosyltransferase gene (SST; EC 2.4.1.99) such that said chimeric gene is capable of transforming a monocot plant cell resulting in production of fructan with no deleterious effect on the said plant cell.

The invention further describes a chimeric gene comprising a tissue specific promoter, operably linked to the coding sequence for a fructan-fructan-fructosyltransferase gene (FFT; EC 2.4.1.100) such that said chimeric gene is capable of transforming a transformed plant cell (harboring a chimeric gene comprising a tissue specific promoter, operably linked to the coding sequence for a sucrose-sucrose-fructosyltransferase gene (SST; EC 2.4.1.99)) resulting in production of fructan, with no deleterious effect on the said plant cell.

The invention also includes a monocot plant transformed with one or both of the chimeric genes described above, such that the plant produces fructan. The invention also concerns a method of producing fructose or fructose polymers comprising growing the plant, harvesting the plant, and extracting fructan from the harvested plant.

The invention further describes a chimeric gene comprising a tissue specific promoter, operably linked to the coding sequence for a sucrose-sucrose-fructosyltransferase gene (SST; EC 2.4.1.99) such that the chimeric gene is capable of transforming a monocot plant cell resulting in production of fructose polymers containing 2 to 3 fructose residues, with no deleterious effect on the transformed plant cell.

The present invention is not limited to naturally occurring fructosyl-transferases but may equally well be performed by using modified versions thereof. Modifications may influence the activity of the fructosyltransferase in such a way that, for example, the degree of polymerization or the structure of the fructan produced is altered. Furthermore, according to the present invention a single fructosyltransferase gene or a combination of fructosyltransferase genes of plant origin may be used.

The induced accumulation of fructans in transgenic plants using the principles described herein will allow for the extraction of fructans from these plants for the purpose of fructan production. Fructans can accumulate in these plants (e.g., in harvestable organs such as roots, leaves, stems and seeds). Furthermore, the present invention further relates to seeds, cuttings or other parts of the transgenic plants which are useful for the continuous production of further generations of said plants.

The fructans produced using transgenic plants of the present invention may be used in various food and non-food applications. Examples include but are not limited to human and animal food products, in the production of fructose syrups, in the production of chemicals and plastics either as such or in a modified form.

Genetically modified crop plants which incorporate the fructosyl-transferase-encoding constructs mentioned above will allow for the efficient production of high quality carbohydrate polymers useful to man.

DETAILED DESCRIPTION OF THE INVENTION

Definitions

Figure 1:
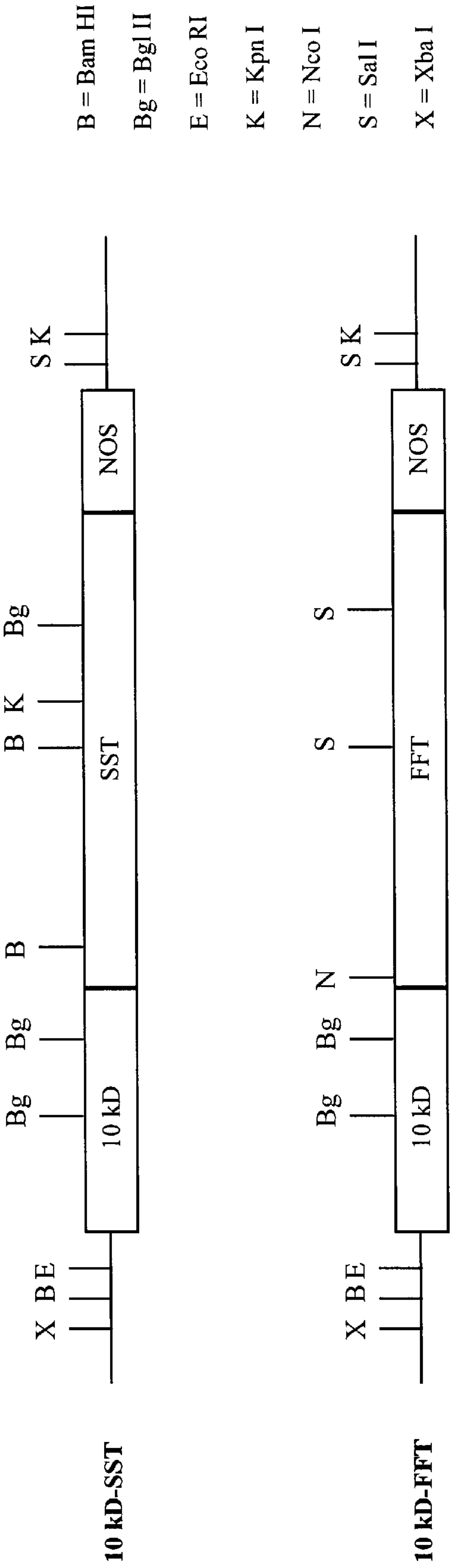
FIG. 1 shows a diagram of the cassettes used to express the Jerusalem artichoke SST and FFT genes (10 kD-SST and 10 kD-FFT, respectively) in transgenic maize endosperm. Each construct also contains the tissue specific 10 kD zein promoter and 3' transcription termination region.

In the context of this disclosure, a number of terms shall be utilized. As used herein, the term "nucleic acid" refers to a large molecule which can be single-stranded or double-stranded, composed of monomers (nucleotides) containing a sugar, phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers.

As used herein, "substantially similar" refers to DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which results in the production of a chemically equivalent amino acid at a given site, are contemplated; thus, a codon for the amino acid alanine, a hydrophobic amino acid, may be substituted by a codon encoding another hydrophobic amino acid residue such as glycine, valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity of the encoded products. Moreover, the skilled artisan recognizes that "substantially similar" sequences encompassed by this invention can also defined by their ability to hybridize, under stringent conditions (0.1×SSC, 0.1% SDS, 65° C.), with the sequences exemplified herein.

"Gene" refers to a nucleic acid fragment that encodes all or a portion of a specific protein, and includes regulatory sequences preceding (5' non-coding) and following (3' non-coding) the coding region. "Native gene" refers to the gene as found in nature with its own regulatory sequences. "Chimeric gene" refers to a gene comprising heterogeneous regulatory and coding sequences. "Endogenous gene" refers to the native gene normally found in its natural location in the genome. A "foreign gene" refers to a gene not normally found in the host organism but that is introduced by gene transfer. "Foreign gene" can also refer to a gene that is normally found in the host organism, but that is reintroduced at a location in the genome where it is not normally found, resulting in one or more additional copies of the coding sequence of an endogenous gene.

"Coding sequence" refers to a DNA sequence that codes for a specific protein and excludes the non-coding sequences.

"Initiation codon" and "termination codon" refer to a unit of three adjacent nucleotides in a coding sequence that specifies initiation and chain termination, respectively, of protein synthesis (mRNA translation). "Open reading frame" refers to the amino acid sequence encoded between translation initiation and termination codons of a coding sequence.

"RNA transcript" refers to the product resulting from RNA polymerase-catalyzed transcription of a DNA sequence. When the RNA transcript is a perfect complementary copy of the DNA sequence, it is referred to as the "primary transcript" or it may be a RNA sequence derived from posttranscriptional processing of the primary transcript. "Messenger RNA" (mRNA) refers to RNA that can be translated into protein by the cell. "cDNA" refers to a double-stranded DNA, one strand of which is complementary to and derived from mRNA by reverse transcription.

As used herein, suitable "regulatory sequences" refer to nucleotide sequences located upstream (5'), within, and/or downstream (3') to a coding sequence, which control the transcription and/or expression of the coding sequences. These regulatory sequences include promoters, translation leader sequences, transcription termination sequences, and polyadenylation sequences. In artificial DNA constructs, regulatory sequences can also control the transcription and stability of antisense RNA.

"Promoter" refers to a DNA sequence in a gene, usually upstream (5') to its coding sequence, which controls the expression of the coding sequence by providing the recognition for RNA polymerase and other factors required for proper transcription. A promoter may also contain DNA sequences that are involved in the binding of protein factors which control the effectiveness of transcription initiation in response to physiological or developmental conditions. It may also contain enhancer elements.

An "enhancer" is a DNA sequence that can stimulate promoter activity. It may be an innate element of the promoter or a heterologous element inserted to enhance the level and/or tissue-specificity of a promoter. "Constitutive" promoters refer to those that direct gene expression in substantially all tissues and demonstrate little temporal or developmental regulation. "Tissue-specific" or "development-specific" promoters as referred to herein are those that direct gene expression almost exclusively in specific tissues, such as leaves or seeds, or at specific developmental stages in a tissue, such as in early or late embryogenesis, respectively.

The term "operably linked" refers to nucleic acid sequences on a single nucleic acid molecule which are associated so that the function of one is affected by the other. For example, a promoter is operably linked with a structural gene (i.e., a gene encoding a fructosyltransferase) when it is capable of affecting the expression of that structural gene (i.e., that the structural gene is under the transcriptional control of the promoter).

The term "expression", as used herein, is intended to mean the production of a functional end-product encoded by a gene. More particularly, "expression" refers to the transcription of the sense (mRNA) or the antisense RNA derived from the nucleic acid fragment(s) of the invention that, in conduction with the protein apparatus of the cell, results in altered levels of protein product. "Altered levels" refers to the production of gene product(s) in transgenic organisms in amounts or proportions that differ from that of normal or non-transformed organisms.

The "3' non-coding sequences" refers to the DNA sequence portion of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

"Transformation" refers to the transfer of a nucleic acid fragment into the genome of a host organism, resulting in genetically stable inheritance. Host organisms containing the transformed nucleic acid fragments are referred to as "transgenic" organisms.

"Fructosyltransferase" refers to a protein coded for by any one of several plant genes having the property of producing a carbohydrate polymer consisting of repeating fructose residues. The repeating fructose residues may be linked by α2-1 linkage or a α2-6 linkage or any combination of the two linkage types. The polymer of repeating fructose residues may contain one terminal glucose residue, derived from a sucrose molecule, and at least two fructose residues. The polymer of repeating fructose residues in any form, with any combination of linkages, and with any number of fructose residues, is referred to generally as a "fructan".

A "fructosyltransferase gene" or "FTF" refers to the DNA sequence coding for a fructosyltransferase protein. The term "deleterious effect" as used herein, refers to a direct or indirect injurious effect on a plant or plant cell as a result of fructan accumulation, such that the plant or plant cell is prevented from performing certain functions including, but not limited to, synthesis and transport of carbohydrates within a cell and throughout the plant, regeneration of transgenic plants or tissue, development of the plant or plant cell to maturity, or the ability to pass the desired trait or traits to progeny.

The present invention describes chimeric genes comprising tissue specific regulatory sequences, FTF coding sequences and a transcription terminating region. The chimeric gene is capable of mediating the synthesis of a fructose polymer using sucrose as a substrate when expressed in a transgenic monocot plant wherein expression of the FTF gene results in the synthesis of novel fructose polymers, useful in numerous in food and industrial applications. A transgenic corn plant (*Zea mays*) properly expressing the FTF gene, distinguishes itself from a generic plant of the same species by the presence of fructan accumulation in the mature seeds.

Transfer of the nucleic acid fragments of this invention into a plant directs expression of the protein in a manner that results in accumulation of this useful polymer, without concern for loss or alteration of the polymer due to plant degratory enzymes during harvest, transport, or storage and without the loss of established co-products from any particular species. Transgenic crops containing chimeric genes comprising tissue specific regulatory sequences, the FTF gene and a transcription termination region will provide a renewable source of small (DP 2–3) and large molecular weight fructose polymers. Accumulation of fructan will be determined in part, by the level of expression of the chimeric gene in transformed crops. The level of expression depends in part, on the tissue specific expression signals, the number of copies of the gene integrated into the plant genome and location of gene integration; fructan accumulation may also be subject to substrate availability. The amount of substrate available to the enzyme depends on the species (including mutants within a species), the tissue type where expression occurs, the subcellular location of expression and on the stage of development of a particular plant. The stability of the introduced protein may also influence fructan accumulation and depends in part, on its proper processing, intracellular targeting and its ability to function in a foreign environment.

Successful expression of a gene with carbohydrate metabolic properties such as the Jerusalem artichoke SST and FFT genes, in a transgenic plant would require consideration of the following factors: (1) the species transformed, (2) the specific tissue where expression is to occur, (3) and the timing of expression. All of these factors must be carefully coordinated in order for production of fructan to occur in a transgenic cell, with no deleterious effect.

Expression of a gene with sucrose metabolizing activity, such as an FTF protein, in a specific transgenic plant species would not necessarily create the same, or even a desired effect when expressed in a different plant species. Differences in carbohydrate profiles among species suggests that an enzyme specific for sucrose will not always have sufficient substrate available to produce the same result when expressed in various species. It is well established that the availability of sucrose as a substrate not only varies greatly from species to species but also in mutants within the same species, (Lampe et al. (1931) *Bot. Gaz.,* 91:337–380).

Mechanisms for sucrose transport and accumulation in tissue also vary greatly from one species to another. Sucrose hydrolysis is an integral part of the import mechanism in developing corn seed, (Porter et al., (1985) *Plant Phys.,* 77:524–531), but is not a prerequisite for transport to developing soybean embryo (Thorne, (1982) *Plant Phys.,* 70:953–958), or to wheat endosperm (Jenner, *Aust. J. Plant Phys.,* 1:319–329 (1974)). Therefore, expression of a FTF in the seed of one species may have access to an abundance of sucrose, however, fructan synthesis in seed of another species could be severely hindered by the accumulation of hexoses sugars in place of sucrose.

Tissue and developmental specific expression of a gene may be intrinsic to the promoter, the 3' non-coding region or combinations of the two, used in chimeric constructs. Promoters utilized to drive gene expression in transgenic plants can be derived from many sources so long as the chosen promoter(s) have sufficient transcriptional activity to accomplish the invention by expressing translatable mRNA in the desired host tissue. Preferred promoters are those that allow expression specifically in seeds. Examples of seed-specific promoters include, but are not limited to, the promoters of seed storage proteins. The seed storage proteins are strictly regulated, being expressed almost exclusively in seeds in a highly organ-specific and stage-specific manner (Higgins et al. (1984) *Ann. Rev. Plant Physiol.* 35:191–221; Goldberg et al. (1989) *Cell* 56:149–160; Thompson et al. (1989) *BioEssays* 10:108–113). Moreover, different seed storage proteins may be expressed at different stages of seed development.

There are currently numerous examples for seed-specific expression of seed storage protein genes in transgenic plants. These include genes from monocots such as for barley β-hordein (Marris et al. (1988) *Plant Mol. Biol.* 10:359–366) and wheat glutenin (Colot et al. (1987) *EMBO J.* 6:3559–3564). Moreover, promoters of seed-specific genes, operably linked to heterologous coding sequences in chimeric gene constructs, also maintain their temporal and spatial expression pattern in transgenic plants. Such examples include linking either the Phaseolin or Arabidopsis 2S albumin promoters to the Brazil nut 2S albumin coding sequence and expressing such combinations in tobacco, Arabidopsis, or *Brassica napus* (Altenbach et al. (1989) *Plant Mol. Biol.* 13:513–522; Altenbach et al. (1992) *Plant Mol. Biol.* 18:235–245; De Clercq et al. (1990) *Plant Physiol.* 94:970–979), bean lectin and bean β-phaseolin promoters to express luciferase (Riggs et al. (1989) *Plant Sci.* 63:47–57), and wheat glutenin promoters to express chloramphenicol acetyl transferase (Colot et al. (1987) *EMBO J.* 6:3559–3564).

Of particular use in the expression of the nucleic acid fragment(s) of the invention will be promoters from several extensively characterized corn seed storage protein genes such as endosperm-specific promoters from the 10 kD zein gene (Kirihara et al. (1988) *Gene* 71:359–370), the 15 kD zein gene (Hoffman et al. (1987) *EMBO J.* 6:3213–3221; Schermthaner et al. (1988) *EMBO J.* 7:1249–1253; Williamson et al. (1988) *Plant Physiol.* 88:1002–1007), the 27 kD zein gene (Prat et al. (1987) *Gene* 52:51–49; Gallardo et al. (1988) *Plant Sci.* 54:211–281), and the 19 kD zein gene (Marks et al. (1985) *J. Biol. Chem.* 260:16451–16459). The relative transcriptional activities of these promoters in corn have been reported (Kodrzyck et al. (1989) *Plant Cell* 1:105–114) providing a basis for choosing a promoter for use in chimeric gene constructs for corn. Moreover, promoters that drive the expression of genes encoding enzymes involved in starch biosythesis may be used in the practice of this invention. These include the 5' regulatory sequences of the sucrose synthase (Yang, N.-S. and Russell, D. (1990) *Proc. Natl. Acad. Sci.* 87:4144–4148) and the waxy or granule-bound starch synthase I (Unger et al. (1991) *Plant Physiol.* 96:124) genes. Promoter elements may be derived from other starch synthase (granule-bound and soluble isoforms) genes when these become available, and from the sh2 (Bhave et al. (1990) *Plant Cell* 2:581–588) and bt2 (Bae et al. (1990) *Maydica* 35:317–322) genes whose products constitute the enzyme ADP-glucose pyrophosphorylase. It is envisioned that the introduction of enhancers or enhancer-like elements into other promoter constructs will also provide increased levels of primary transcription to accomplish the invention. These would include viral enhancers such as that found in the 35S promoter (Odell et al. (1988) *Plant Mol. Biol.* 10:263–272), enhancers from the opine genes (Fromm et al. (1989) *Plant Cell* 1:977–984), or enhancers from any other source that result in increased transcription when placed into a promoter operably linked to the nucleic acid fragment of the invention.

Introns isolated from the maize Adh-1 and Bz-1 genes (Callis et al. (1987) *Genes Dev.* 1:1183–1200), and intron 1 and exon 1 of the maize Shrunken-1 (sh-1) gene (Maas et al. (1991) *Plant Mol. Biol.* 16:199–207) may also be of use to increase expression of introduced genes. Results with the first intron of the maize alcohol dehydrogenase (Adh-1) gene indicate that when this DNA element is placed within the transcriptional unit of a heterologous gene, mRNA levels can be increased by 6.7-fold over normal levels. Similar levels of intron enhancement have been observed using intron 3 of a maize actin gene (Luehrsen, K. R. and Walbot, V. (1991) *Mol. Gen. Genet.* 225:81–93). Enhancement of gene expression by Adh1 intron 6 (Oard et al. (1989) *Plant Cell Rep* 8:156–160) has also been noted. Exon 1 and intron 1 of the maize sh-1 gene have been shown to individually increase expression of reporter genes in maize suspension cultures by 10 and 100-fold, respectively. When used in combination, these elements have been shown to produce up to 1000-fold stimulation of reporter gene expression (Maas et al. (1991) *Plant Mol. Biol.* 16:199–207).

Any 3' non-coding region capable of providing a polyadenylation signal and other regulatory sequences that may be required for proper expression can be used to accomplish the invention. This would include the 3' end from any storage protein such as the 3' end of the 10 kd, 15 kd, 27 kd and alpha zein genes, the 3' end of the bean phaseolin gene, the 3' end of the soybean β-conglycinin gene, the 3' end from viral genes such as the 3' end of the 35S or the 19S cauliflower mosaic virus transcripts, the 3' end from the opine synthesis genes, the 3' ends of ribulose 1,5-bisphosphate carboxylase or chlorophyll a/b binding protein, or 3' end sequences from any source such that the sequence employed provides the necessary regulatory information within its nucleic acid sequence to result in the proper expression of the promoter/coding region combination to which it is operably linked. There are numerous examples in the art that teach the usefulness of different 3' non-coding regions (for example, see Ingelbrecht et al. (1989) *Plant Cell* 1:671–680).

A number of genes from plant sources encoding enzymes with FTF activity have been isolated and sequenced. These include the SST and FFT genes from onion (*Allium cepa* L.), barley (*Hordeum vulgare* L.) and Jerusalem artichoke (*Helianthus tuberosus*); (Vijn et al., (1997) *Plant J.* 11:387–398; Sprenger et al., (1997) *Febs Lett.* 400:355–358; Van Tunen et al., WO 96/21023; Smeekens et al., WO 96/01904). Preferred among these are the plant-derived SST and FFT genes from Jerusalem artichoke.

The SST and FFT genes can be isolated by techniques routinely employed by the skilled artisan for isolation of genes when the nucleotide sequence of the desired gene is known, or when the sequence of a homologous gene from another organism is known. Sequence information about the desired gene can be used to prepare oligonucleotide probes for identification and isolation of the entire gene from an appropriate genetic library. This library may be a genomic library, wherein the coding region may be contained on a single DNA fragment or may be contained on several distinct DNA fragments. Alternatively, the library may be a cDNA library wherein the likelihood of isolating a cDNA clone comprising the entire coding region as one contiguous sequence is greater. In either instance, the appropriate clone (s) can be identified by DNA-DNA hybridization with probes corresponding to one or more portions of the desired genes. Alternatively, oligonucleotide primers can be prepared and employed as PCR primers in order to amplify and subsequently isolate all or part of the coding region from genomic DNA, or from the genomic or cDNA libraries described above.

Several different assays can be used to detect expression of the chimeric genes in seeds of the transformed plants. RNA transcripts, specific to the FTF genes may be detected by Southern or northern analysis. The FTF protein can be extracted, detected and quantified immunologically by methods known to those skilled in the art. Alternatively seed tissue may be ground and extracted with a polar solution, isolating and concentrating polysaccharides, including fructans, which can then be detected by: TLC analysis, combined with a kestose specific stain (Wise et al., (1955) *Anal. Chem.* 27:33–36); HPLC analysis using fructan standards (Chatterton et al. (1993) In: Fuchs A. ed *Inulin and inulin-containing crops*. Elsevier, Amsterdam pp. 93–99); or hydrolysis followed and an enzymatic-linked assay (Brown, C. and Huber, S. (1987) *Physiol. Plant* 70:537–543).

Various methods of introducing a DNA sequence (chimeric constructs containing SST or SST/FFT genes) into eukaryotic cells (i.e., transformation) of higher plants are available to those skilled in the art (see EPO publications 0 295 959 A2 and 0 138 341 A1). Such methods include high-velocity ballistic bombardment with metal particles coated with the nucleic acid constructs (see Klein et al. (1987) *Nature* (London) 327:70–73, and see U.S. Pat. No. 4,945,050), as well as those based on transformation vectors based on the Ti and Ri plasmids of Agrobacterium spp., particularly the binary type of these vectors. Ti-derived vectors transform a wide variety of higher plants, including monocotyledonous and dicotyledonous plants, such as soybean, cotton and rape (Pacciotti et al. (1985) *Bio/Technology* 3:241; Byrne et al. (1987) *Plant Cell, Tissue and Organ Culture* 8:3; Sukhapinda et al. (1987) *Plant Mol. Biol.* 8:209–216; Lorz et al. (1985) *Mol. Gen. Genet.* 199:178–182; Potrykus et al. (1985) *Mol. Gen. Genet.* 199:183–188).

Other transformation methods for chimeric constructs containing SST or SST/FFT genes are available to those skilled in the art, such as direct uptake of foreign DNA constructs (see EPO publication 0 295 959 A2), and techniques of electroporation (see Fromm et al. (1986) *Nature* (London) 319:791–793). Once transformed, the cells can be regenerated by those skilled in the art. Also relevant are several recently described methods of introducing nucleic acid fragments into commercially important crops, such as rapeseed (see De Block et al. (1989) *Plant Physiol.* 91:694–701), sunflower (Everett et al., (1987) *Bio/Technology* 5:1201–1204), soybean (McCabe et al. (1988) *Bio/Technology* 6:923–926; Hinchee et al. (1988) *Bio/Technology* 6:915–922; Chee et al. (1989) *Plant Physiol.* 91:1212–1218; Christou et al. (1989) *Proc. Natl. Acad. Sci USA* 86:7500–7504; EPO Publication 0 301 749 A2), and corn (Gordon-Kamm et al. (1990) *Plant Cell* 2:603–618; Fromm et al. (1990) *Bio/Technology* 8:833–839). One skilled in the art is familiar with still other means for the production of transgenic maize plants including introduction of DNA into protoplasts and regeneration of plants from said protoplasts (Omirulleh et al. (1993) *Plant Mol. Biol.* 21:415–423), electroporation of intact tissues (D'Hulluin et al. (1992) *Plant Cell* 4:1495–1505; Laursen et al. (1994) *Plant Mol. Biol.* 24:51–61), silica carbide mediated fiber transformation of maize cells (Kaeppler et al. (1992) *Theor. Appl. Genet.* 84:560–566; Frame et al. (1994) *Plant J.* 6:941–948). In addition to the method of particle bombardment of maize callus cells described above, one skilled in the art is familiar with particle bombardment of maize scutellar or suspension cultures to yield fertile transgenic plants (Koziel et al. (1993) *Bio/Technology* 11:194–200; Walters et al. (1992) *Plant Mol. Biol.* 18:189–200).

Once transgenic plants are obtained by one of the methods described above, it will be necessary to screen individual transgenics for those that most effectively display the desired phenotype. It is well known to those skilled in the art that individual transgenic plants carrying the same construct may differ in expression levels; this phenomenon is commonly referred to as "position effect". For example, when the construct in question is designed to express higher levels of the gene of interest, individual plants will vary in the amount of the protein produced and thus in enzyme activity; this in turn will effect the phenotype. This should not be seen as a limitation on the present invention, but instead as practical matter that is appreciated and anticipated by the person skilled in this art. Accordingly, skilled artisan will develop methods for screening large numbers of transformants. The nature of these screens will generally be chosen on practical grounds, and is not an inherent part of the invention.

EXAMPLES

The present invention is further defined in the following examples. It will be understood that the examples are given for illustration only and the present invention is not limited to uses described in the examples. The present invention can be used to generate transgenic corn plants whose seed carbohydrate profile is altered by accumulation of fructose polymers and where its properties are useful such as in, but not limited to, foods, paper, plastics, adhesives, or paint. From the above discussion and the following examples, one skilled in the art can ascertain, and without departing from the spirit and scope thereof, can make various changes and modifications of the invention to adapt it to various usages and conditions. All such modifications are intended to fall within the scope of the intended claims.

Example 1

Chimeric Construct for Expression of the Jerusalem Artichole SST Gene in Transgenic *Zea mays* L.

A construct designed for tissue specific expression of the Jerusalem artichoke SST gene in maize endosperm was assembled by replacing the Cauliflower Mosaic Virus (CaMV) 35S promoter in the plasmid pSST403 (Van Tunen et al., WO 96/21023) with a maize endosperm-specific 10 kD zein, seed storage gene promoter (Kirihara et al. (1988) *Gene* 71:359–370). The nucleotide sequence of the Herusalem artichoke SST gene is shown in SEQ ID NO:5, and the amino acid sequence of the protein encoded by this gene is shown in SEQ ID NO:6. The complete SST coding sequence contained in pSST403 (Van Tunen et al., WO 96/21023) was isolated by digesting with the restriction endonuclease enzymes NcoI and HindIII. The isolated sequence was added to the plasmid pCyt-SacB (Caimi et al. (1996) *Plant Physiol.* 110:355–363) containing a 10 kD zein promoter and 3' termination region. The maize endosperm expression cassette, containing the 10 Kd promoter, SST coding sequence (including the native secretory and vacuole targeting signals) and the 10 kD 3' end, designated 10 kD-SST (FIG. 1), was isolated by digesting with SmaI and SalI, then ligated into the plasmid KS17. The KS17 vector contains a hygromycin resistance gene (HPT) used as the selectable marker. The final vector was designated 10 kD-SST-17 was used directly for transformation into corn by particle bombardment.

Plant Material and Transformation

The plant expression vector 10 kD-SST-17 and a plasmid vector encoding a selectable marker (pDetric) were cotransformed into embryogenic corn callus derived from crosses of the inbred lines A188 and B73 (Armstrong et al.(1991) *Maize Genetics Cooperation Newsletter* 65:92–93) by microprojectile bombardment (Klein et. al., (1987) *Nature* 327:70–73). Transformed embryogenic cells were recovered on medium containing either glufosinate-ammonium or chlorsulfuron. The selectable marker pDetric contains the BAR gene (Thompson et al. (1987) *The EMBO Journal* 6:2519–2523), coding for phosphinothricin acetyltransferase, under the control of the 35S promoter. pALSLUC (Fromm, et al, (1990) *Biotechnology* 8:833–839), a plasmid vector encoding a mutant acetolactate synthase (ALS) gene that confers resistance to chlorsulfuron could also be used as a selectable marker. Expression of the mutant ALS gene is regulated by the CaMV 35S promoter. Transgenic shoots were transferred to 12 inch pots containing METROMIX™ (Scotts-Sierra company) soil and grown to maturity in the greenhouse. Mature $R_1$ seed from original transformants were grown in the greenhouse or planted directly in the field.

Analysis of Transgenic Plants Expressing the SST Gene

Detection of the SST gene in transgenic plants was accomplished by PCR analysis, using oligonucleotide primers specific for the SST gene:

```
SST-1: 5'-ATGAATCCTTTCATCCACCACGACCACCCCTCTC-3'   (SEQ ID NO:1)

SST-2: 5'-CCCAGGAAGAGGGAAAGGATTGAGTTCTGCTTCCCC-3'  (SEQ ID NO:2)
```

Figure 2:
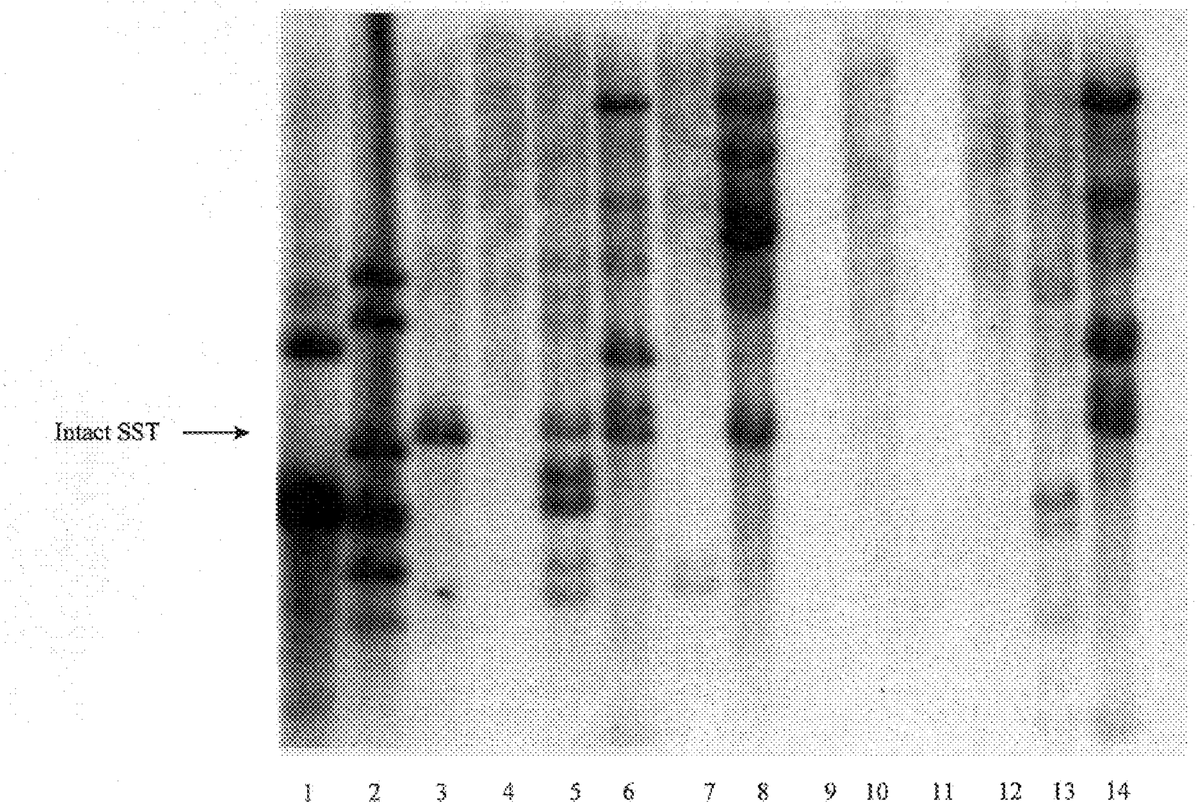
FIG. 2 shows Southern Blot analysis of leaf tissue from fourteen independently transformed lines containing only the 10 kD-SST cassette. Genomic DNA was digested with the restriction enzyme Bgl II. The complete 2.0 Kb coding sequence of the SST gene was labeled with $^{32}P$ and used to probe genomic DNA that was previously transferred to nylon membranes. Multiple intact (indicated by the arrow) and rearranged copies of the SST gene were shown to be present in several of the transgenic maize lines.

Confirming the presence of the SST gene in transgenic tissue and estimating the copy number was done by Southern Blot analysis, using the complete 2.0 Kb SST coding sequence. Southern analysis demonstrated the presence of multiple intact and rearranged copies of the SST gene in transgenic lines (FIG. 2).

Carbohydrate Analysis of Transgenic Maize Lines Containing the SST Gene

Figure 3:
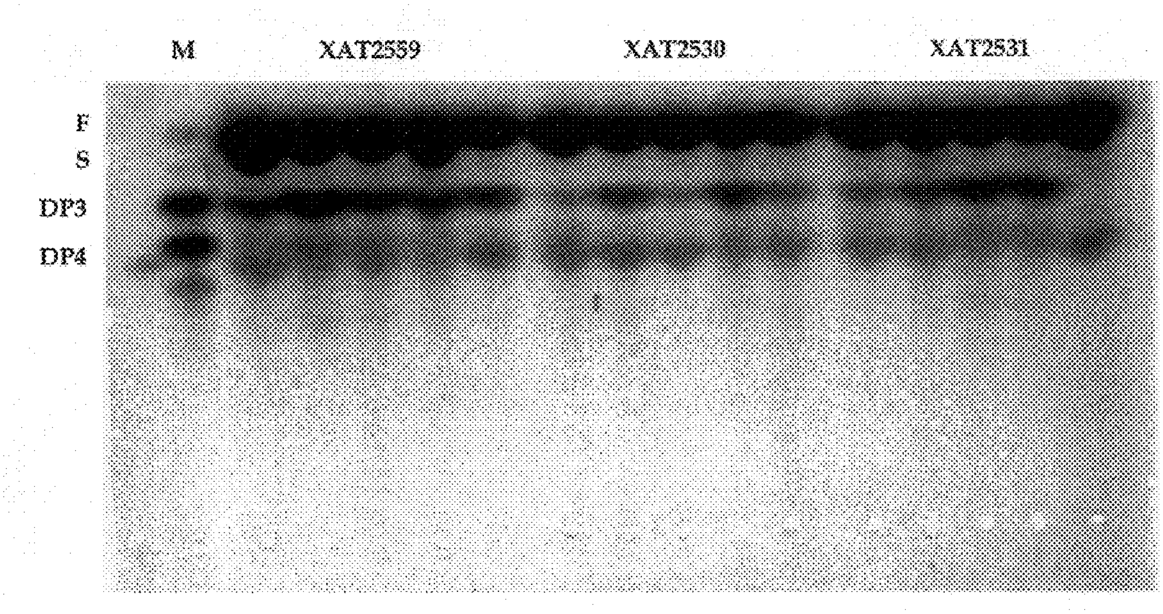
FIG. 3 shows TLC analysis of individual seeds from three transgenic lines containing intact copies of the 10 kD-SST expression cassette. Fructose, F; Sucrose, S; and fructan polymers containing 1 or 2 additional fructose residues (DP3 and DP4, respectively) are indicated. A marker lane (M) containing fructose, sucrose, DP3 and DP4 fructans is also indicated.

Individual seeds from transgenic lines were harvested at 25–35 days post-pollination (DPP) for detection of fructose polymers. The seeds were crushed with a mortar and pestle. A small amount of water (200–400 uL) was added and the mixture heated to 80° C. for 10 minutes. The homogenized tissue was centrifuged at 10,000×g for 10 minutes and 2 uL of aqueous solution spotted on HP-K silica TLC plates (Whatman Scientific, Clifton, N.J.). TLC plates were developed twice in butanol:propanol:water (3:14:4). Fructan was detected by urea-phosphoric acid stain (Wise et al. (1955) *Anal. Chem.* 27:33–36). Analysis demonstrated that control seeds (untransformed) did not contain fructan. TLC plates also demonstrated that seeds expressing the SST gene accumulated fructan with a degree of polymerization (DP) of 3 (FIG. 3).

Example 2

Chimeric Construct for Expression of the Jerusalem Artichole FFT Gene in Transgenic *Zea mays* L.

A construct designed for tissue specific expression of the Jerusalem artichoke FFT gene in maize endosperm was assembled by replacing the Cauliflower Mosaic Virus (CaMV) 35S promoter in the plasmid pSST405 (Van Tunen et al., WO 96/21023) with a maize endosperm-specific 10 kD zein, seed storage gene promoter (Kirihara et al. (1988) *Gene* 71:359–370). The nucleotide sequence of the Jerusalem artichoke FFT gene is shown in SEQ ID NO:7, and the amino acid sequence of the protein encoded by this gene is shown in SEQ ID NO:8. The complete FFT coding sequence contained in pSST405 (Van Tunen et al., WO 96/21023) was isolated by digesting with the restriction endonuclease enzymes NcoI and BamHI. The isolated sequence was added to the plasmid pCyt-SacB (Caimi et al. (1996) *Plant Physiol.* 110:355–363) containing a 10 kD zein promoter and 3' termination region. PCyt-SacB was digested was NcoI and BamHI to remove the SacB region. The maize endosperm expression cassette, containing the 10 Kd promoter, FFT coding sequence (including the native secretory and vacuole targeting signals) and the 10 kD 3' end, designated 10 kD-FFT (FIG. 1), was isolated by digesting with SmaI and SalI, then ligated into the plasmid KS17. The final vector was designated 10 kD-FFT-17 was used directly for transformation into corn by particle co-bombardment with the plasmid 10 kD-SST-17, and pDetric described in Example 1. Transformation, regeneration and growth to mature plants was by the methods described in Example 1.

Analysis of Transgenic Plants Expressing the SST and FFT Genes

Detection of the FFT gene in transgenic plants co-bombarded with SST and FFT genes was accomplished by PCR analysis, using oligonucleotide primers specific for the FFT coding sequence:

```
FFT-1: 5'-CCCCTGAACCCTTTACAGACCTTGAACATGAACCCCA-3'  (SEQ ID NO:3)

FFT-2: 5'-GGGCGGAAATCTTGAGAGATGCTTTCACACTCGTACC-3'  (SEQ ID NO:4)
```

Figure 4:
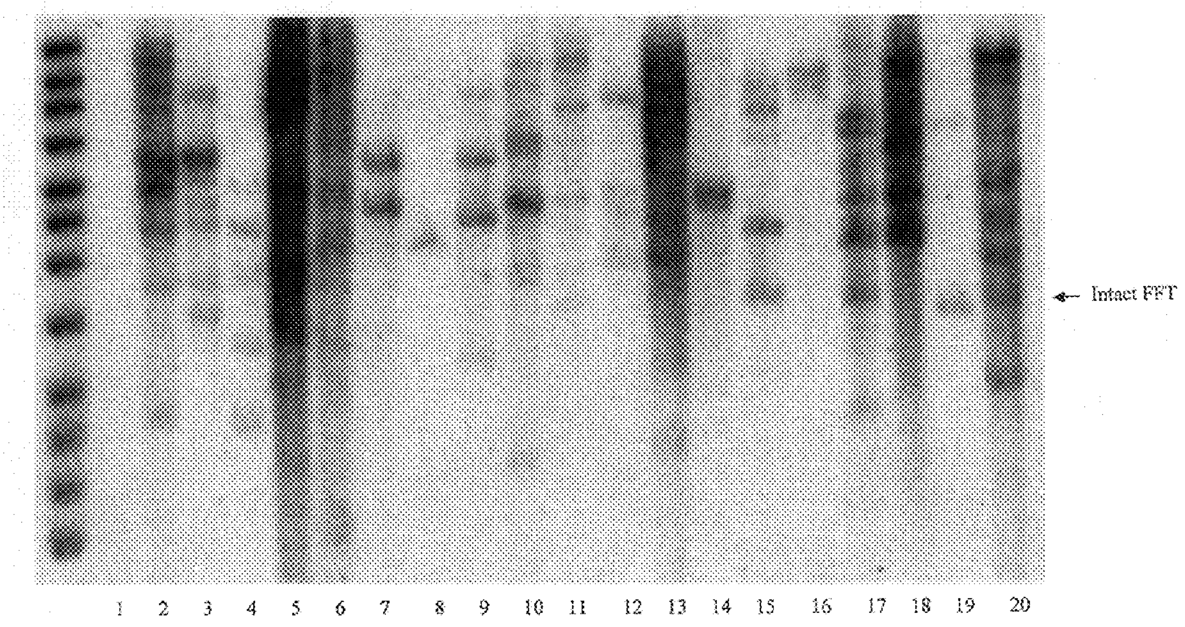
FIG. 4 shows Southern Blot analysis of leaf tissue from twenty independent transformed lines containing the 10 kD-SST and 10 kD-FFT cassettes. DNA from lines previously shown to contain at least one intact copy of the 10 kD-SST cassette were digested with the restriction enzymes Eco RI and Bam HI. The complete coding sequence of the FFT gene was labeled with $^{32}P$ and used to re-probe genomic DNA. Multiple intact (indicated by the arrow) and rearranged copies of the FFT gene were shown to be present in several of the transformed lines.

Confirming the presence of the FFT gene in transgenic tissue and estimating the copy number was done by Southern analysis, using the complete 2.0 Kb FFT coding sequence. Southern analysis demonstrated the presence of multiple intact and rearranged copies of the FFT gene in transgenic lines (FIG. 4).

Carbohydrate Analysis of Maize Lines Containing the SST and FFT Genes

Figure 5:
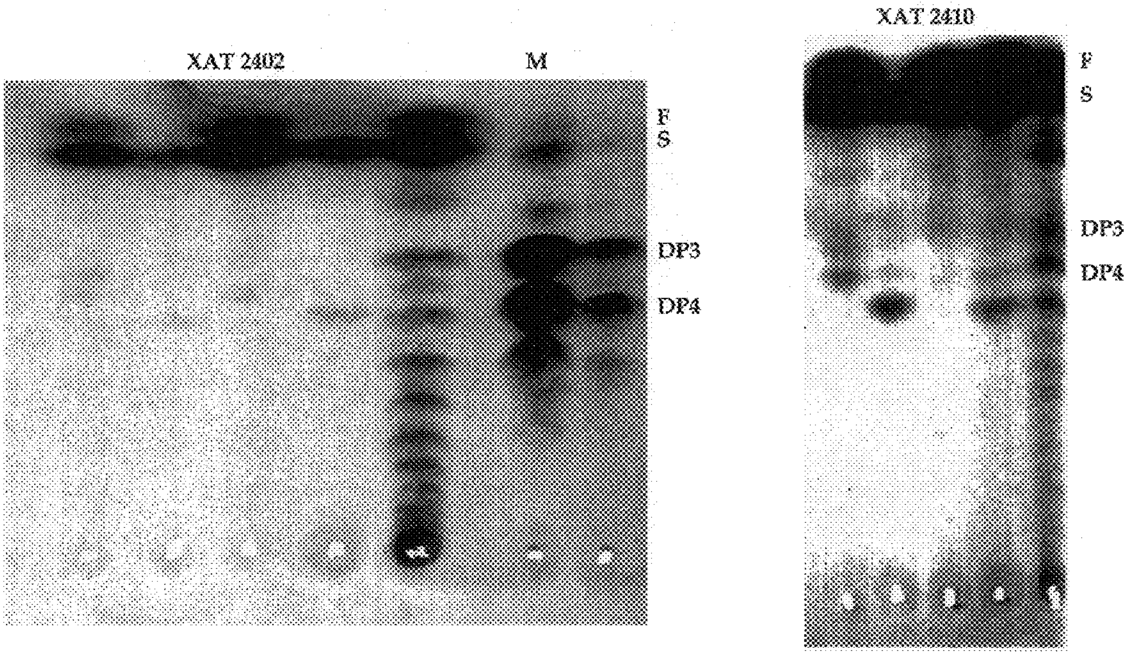
FIG. 5 shows TLC analysis of individual seeds from two transgenic lines containing intact copies of both the 10 kD-SST and 10 kD-FFT expression cassettes. Fructose polymers, larger than DP3 were demonstrated in seeds from each of the two lines. Fructose, F; Sucrose, S; and fructan polymers containing 1 and 2 additional fructose residues (DP3 and DP4, respectively) are indicated. A marker lane (M) containing fructose, sucrose, DP3 and DP4 fructans is indicated.

Transgenic seeds expressing the SST and FFT genes were harvested at 25–35 DPP. Isolation and detection of fructan was described in Example 1. Fructan was detected by urea-phosphoric acid stain (Wise et al. (1955) *Anal. Chem.* 27:33–36). Analysis demonstrated that control seeds did not contain fructan. TLC plates also demonstrated that seeds expressing both the SST and FFT genes accumulated fructan with a DP much larger than in lines containing the SST gene alone (FIG. 5). The results demonstrate that the FFT gene acts as a chain elongation factor, synthesizing fructan with a DP of at least 20 (the limit of detection by TLC) in transgenic seeds.

What is claimed is:

1. A method for increasing the level of fructan that accumulates in the cells of a transgenic monocot plant comprising:

a) preparing at least one chimeric gene comprising a nucleotide sequence encoding a plant fructosyltransferase, wherein the nucleotide sequence encoding a plant fructosyltransferase is operably linked to suitable regulatory sequences that function in monocot cells;

b) transforming a monocot cell with the at least one chimeric gene; and c) regenerating a transgenic monocot plant from the transformed monocot cell, wherein the level of fructan that accumulates in the cells of the transgenic monocot plant is increased when compared to the level of fructan that accumulates in the cells of a monocot plant comprised of cells that do not contain the at least one chimeric gene, wherein the plant fructosyltransferase is a sucrose-sucrose-fructosyltransferase having the designation EC 2.4.1.99 or a fructose-fructose-fructosyltransferase having the designation EC 2.4.1.100, wherein the nucleotide sequence encoding the sucrose-sucrose-fructosyltransferase is capable of hybridizing to the complement of the nucleotide sequence of SEQ ID NO:5 in a solution containing 0.1×SSC and 0.1% SDS at 65° C., and wherein the nucleotide sequence encoding the fructose-fructose-fructosyltransferase is capable of hybridizing to the complement of the nucleotide sequence of SEQ ID NO:7 in a solution containing 0.1×SSC and 0.1% SDS at 650° C.

2. The method of claim 1, wherein the plant fructosyltransferase is a sucrose-sucrose-fructosyltransferase having the designation EC 2.4.1.99.

3. The method of claim 1, wherein the monocot cell is transformed with a chimeric gene comprising a nucleotide sequence encoding a sucrose-sucrose-frucltosyltransferase having the designation EC 2.4.1.99 and a chimeric gene comprising a nucleotide sequence encoding a fructose-fructose-fructosyltransferase having the designation EC 2.4.1.100.

4. The method of claim 1 wherein the suitable regulatory sequences comprise a tissue specific promoter.

5. The method of claim 4 wherein the tissue specific promoter is a seed specific promoter.

6. The method of claim 1 wherein the transgenic monocot plant is *Zea mays.*

7. The transgenic monocot plant produced by the method of claim 1.

8. A seed from the plant of claim 7.

9. The method of claim 1, wherein the fructan that accumulates in the cells of the transgenic monocot plant has a degree of polymerization of at least 20.

10. A transgenic monocot plant comprising a chimeric gene, wherein the chimeric gene comprises a nucleotide sequence encoding a plant fructosyltransferase, wherein the nucleotide sequence encoding a plant fructosyltransferase is operably linked to suitable regulatory sequences that function in monocot cells, wherein the plant fructosyltransferase is a sucrose-sucrose-fructosyltransferase having the designation EC 2.4.1.99 or a fructose-fructose-fructosyltransferase having the designation EC 2.4.1.100, wherein the nucleotide sequence encoding the sucrose-sucrose-fructosyltransferase is capable of hybridizing to the complement of the nucleotide sequence of SEQ ID NO:5 in a solution containing 0.1×SSC and 0.1% SDS at 65° C., and wherein the nucleotide sequence encoding the fructose-fructose-fruclcosyltransferase is capable of hybridizing to the complement of the nucleotide sequence of SEQ ID NO:7 in a solution containing 0.1×SSC and 0.1% SDS at 65° C.

11. The plant of claim 10, wherein the sucrose-sucrose-fructosyltransferase having the designation EC 2.4.1.99 is a Jerusalem artichoke sucrose-sucrose-fructosyltransferase, and wherein the fructose-fructose-fructosyltransferase having the designation EC 2.4.1.100 is a Jerusalem artichoke fructose-fructose-fructosyltrensferase.

12. The plant of claim 10, wherein the sucrose-sucrose-fructosyltransferase having the designation EC 2.4.1.99 comprises the amino acid sequence of SEQ ID NO:6, and wherein the fructose-fructose-fructosyltransferase having the designation EC 2.4.1.100 comprises the amino acid sequence of SEQ ID NO:8.

13. The plant of claim 10, wherein the nucleotide sequence encoding the sucrose-sucrose-fructosyltransferase comprises the nucleotides sequence of SEQ ID NO:5, and wherein the nucleotide sequence encoding the fructose-fructose-fructosyltransferase comprises the nucleotide sequence of SEQ ID NO:7.

14. The plant of claim 10 containing a chimeric gene comprising a nucleotide sequence encoding a sucrose-sucrose-fructosyltransferase having the designation EC 2.4.1.99 and a chimeric gene comprising a nucleotide sequence encoding a fructose-fructose-fructosyltransferase having the designation EC 2.4.1.100.

15. A transgenic monocot seed comprising a chimeric gene, wherein the chimeric gene comprises a nucleotide sequence encoding a plant fructosyltransferase, wherein the nucleotide sequence encoding a plant fructosyltransferase is operably linked to suitable regulatory sequences that function in monocot cells, wherein the plant fructosyltransferase is a sucrose-sucrose-fructosyltransferase having the designation EC 2.4.1.99 or a fructose-fructose-fructosyltransferase having the designation EC 2.4.1.100, wherein the nucleotide sequence encoding the sucrose-sucrose-fructosyltransferase is capable of hybridizing to the complement of the nucleotide sequence of SEQ ID NO:5 in a solution containing 0.1×SSC and 0.1% SDS at 65° C., and wherein the nucleotide sequence encoding the fructose-fructose-fructosyltransferase is capable of hybridizing to the complement of the nucleotide sequence of SEQ ID NO:7 in a solution containing 0.1×SSC and 0.1% SDS at 65° C.

16. The seed of claim 15, wherein the sucrose-sucrose-fructosyltransferase having the designation ESC 2.4.1.99 is a Jerusalem artichoke sucrose-sucrose-fructosyltransferase, and wherein the fructose-fructose-fructosyltransferase having the designation EC 2.4.1.1.00 is a Jerusalem artichoke fructose-fructose-fructosyltransferase.

17. The seed of claim 15, wherein the sucrose-sucrose-fructosyltransferase having the designation EC 2.4.1.99 comprises the amino acid sequence of SEQ ID NO:6, and wherein the fructose-fructose-fructosyltransferase having the designation EC 2.4.1.100 comprises the amino acid sequence of SEQ ID NO:8.

18. The seed of claim 15, wherein the nucleotide sequence encoding the sucrose-sucrose-fructosyltransferase comprises the nucleotide sequence of SEQ ID NO:5, and wherein the nucleotide sequence encoding the fructose-fructose-fructosyltransferase comprises the nucleotide sequence of SEQ ID NO:7.

19. The seed of claim 15 containing a chimeric gene comprising a nucleotide sequence encoding a sucrose-sucrose-fructosyltransferase having the designation EC 2.4.1.99 and a chimeric gene comprising a nucleotide sequence encoding a fructose-fructose-fructosyltransferase having the designation EC 2.4.1.100.

* * * * *

UNITED STATES PATENT AND TRADEMARK OFFICE

CERTIFICATE OF CORRECTION

PATENT NO. : 6,365,800 B1 Page 1 of 1
DATED : April 2, 2002
INVENTOR(S) : Caimi Perry G.

It is certified that error appears in the above-identified patent and that said Letters Patent is hereby corrected as shown below:

Column 27,
Lines 26 and 65, please delete “65° C.” and substitute therefore -- 65°C --.
Line 30, please delete “$650^{0}$C” and substitute therefore --$65^{0}$C--.
Column 28,
Lines 2, 39 and 43, please delete “65° C.” and substitute therefore -- 65°C --.

Signed and Sealed this

Twenty-fourth Day of August, 2004

JON W. DUDAS
*Director of the United States Patent and Trademark Office*

SEQUENCE LISTING

```
<160> NUMBER OF SEQ ID NOS:  8

<210> SEQ ID NO 1
<211> LENGTH: 34
<212> TYPE: DNA
<213> ORGANISM: PCR Primer

<400> SEQUENCE: 1

atgaatcctt tcatccacca cgaccacccc tctc                                34


<210> SEQ ID NO 2
<211> LENGTH: 36
<212> TYPE: DNA
<213> ORGANISM: PCR Primer

<400> SEQUENCE: 2

cccaggaaga gggaaaggat tgagttctgc ttcccc                              36


<210> SEQ ID NO 3
<211> LENGTH: 37
<212> TYPE: DNA
<213> ORGANISM: PCR Primer

<400> SEQUENCE: 3

cccctgaacc ctttacagac cttgaacatg aacccca                             37


<210> SEQ ID NO 4
<211> LENGTH: 37
<212> TYPE: DNA
<213> ORGANISM: PCR Primer

<400> SEQUENCE: 4

gggcggaaat cttgagagat gctttcacac tcgtacc                             37


<210> SEQ ID NO 5
<211> LENGTH: 2116
<212> TYPE: DNA
<213> ORGANISM: Helianthus tuberosus

<400> SEQUENCE: 5

ggcacgagaa aaaaccctcc ctcaggccac cacatgatgg cttcatccac caccaccacc     60

cctctcattc tccatgatga ccctgaaaac ctcccagaac tcaccggttc tccgacaact    120

cgtcgtctat ccatcgcaaa agtgctttcg gggatccttg tttcggttct ggttataggt    180

gctcttgttg ctttaatcaa caaccaaaca tatgaatccc cctcggccac cacattcgta    240

actcagttgc caaatattga tctgaagcgg gttccaggaa agttggattc gagtgctgag    300

gttgaatggc aacgatccac ttatcatttt caacccgaca aaaatttcat tagcgatcct    360
```

-continued gatggcccaa tgtatcacat gggatggtat catctatttt atcagtacaa ccctcaatct 420
gccatctggg gcaacatcac atggggccac tcggtatcga aagacatgat caactggttc 480
catctccctt tcgccatggt tcctgaccat tggtacgaca tcgaaggtgt catgacgggt 540
tcggctacag tcctccctaa tggtcaaatc atcatgcttt actcgggcaa cgcgtatgat 600
ctctcccaag tacaatgctt ggcgtacgct gtcaactcgt cggatccact tcttatagag 660
tggaaaaaat atgaaggtaa ccctgtctta ctcccaccac caggagtagg ctacaaggac 720
tttcgggacc catccacatt gtggtcgggc cctgatggtg aatatagaat ggtaatgggg 780
tccaagcaca acgagactat tggctgtgct ttgatttacc ataccactaa ttttacgcat 840
tttgaattga aagaggaggt gcttcatgca gtcccacata ctggtatgtg ggaatgtgtt 900
gatctttacc cggtgtccac cgtacacaca aacgggctgg acatggtgga taacgggcca 960
aatgttaagt acgtgttgaa acaaagtggg gatgaagatc gccatgattg gtatgcaatt 1020
ggaagttacg atatagtgaa tgataagtgg tacccagatg acccggaaaa tgatgtgggt 1080
atcggattaa gatatgattt tggaaaattt tatgcgtcca agacgtttta tgaccaacat 1140
aagaagagga gagtcctttg ggctatgtt ggagaaaccg atccccaaaa gtatgacctt 1200
tcaaagggat gggctaacat tttgaatatt ccaaggaccg tcgttttgga cctcgaaact 1260
aaaaccaatt tgattcaatg gccaatcgag gaaaccgaaa accttaggtc gaaaaagtat 1320
gatgaattta aagacgtcga gcttcgaccc ggggcactcg ttccccttga gataggcaca 1380
gccacacagt tggatatagt tgcgacattc gaaatcgacc aaaagatgtt ggaatcaacg 1440
ctagaggccg atgttctatt caattgcacg actagtgaag gctcggttgc aaggagtgtg 1500
ttgggaccgt ttggtgtggt ggttctagcc gatgcccagc gctccgaaca acttcctgta 1560
tacttctata tcgcaaaaga tattgatgga acctcacgaa cttatttttg tgccgacgaa 1620
acaagatcat ccaaggatgt aagcgtaggg aaatgggtgt acggaagcag tgttcctgtc 1680
ctcccaggcg aaaagtacaa tatgaggtta ttggtggatc attcgatagt agagggattt 1740
gcacaaaacg ggagaaccgt ggtgacatca agagtgtatc caacaaaggc gatctacaac 1800
gctgcgaagg tgtttttgtt caacaacgcg actggaatca gtgtgaaggc gtcgatcaag 1860
atctggaaga tgggggaagc agaactcaat cctttccctc ttcctgggtg gactttcgaa 1920
ctttgatggt tatattttgg accctatata tgtgttatta tcatgatggt tatattttgg 1980
accctatata tgtgttatta tcatgaagca taagtttgga ctggaggggg tattattgta 2040
attttatatg catgttctat tacttgtgag gttatagtat gtaattaaat tattatatac 2100
tatatcaatt tctaat 2116

<210> SEQ ID NO 6
<211> LENGTH: 630
<212> TYPE: PRT
<213> ORGANISM: Helianthus tuberosus

<400> SEQUENCE: 6

Met Met Ala Ser Ser Thr Thr Thr Thr Pro Leu Ile Leu His Asp Asp
1 5 10 15

Pro Glu Asn Leu Pro Glu Leu Thr Gly Ser Pro Thr Thr Arg Arg Leu
20 25 30

Ser Ile Ala Lys Val Leu Ser Gly Ile Leu Val Ser Val Leu Val Ile
35 40 45

Gly Ala Leu Val Ala Leu Ile Asn Asn Gln Thr Tyr Glu Ser Pro Ser
50 55 60

-continued

```
Ala Thr Thr Phe Val Thr Gln Leu Pro Asn Ile Asp Leu Lys Arg Val
 65                 70                  75                  80

Pro Gly Lys Leu Asp Ser Ser Ala Glu Val Glu Trp Gln Arg Ser Thr
                85                  90                  95

Tyr His Phe Gln Pro Asp Lys Asn Phe Ile Ser Asp Pro Asp Gly Pro
            100                 105                 110

Met Tyr His Met Gly Trp Tyr His Leu Phe Tyr Gln Tyr Asn Pro Gln
        115                 120                 125

Ser Ala Ile Trp Gly Asn Ile Thr Trp Gly His Ser Val Ser Lys Asp
    130                 135                 140

Met Ile Asn Trp Phe His Leu Pro Phe Ala Met Val Pro Asp His Trp
145                 150                 155                 160

Tyr Asp Ile Glu Gly Val Met Thr Gly Ser Ala Thr Val Leu Pro Asn
                165                 170                 175

Gly Gln Ile Ile Met Leu Tyr Ser Gly Asn Ala Tyr Asp Leu Ser Gln
            180                 185                 190

Val Gln Cys Leu Ala Tyr Ala Val Asn Ser Ser Asp Pro Leu Leu Ile
        195                 200                 205

Glu Trp Lys Lys Tyr Glu Gly Asn Pro Val Leu Leu Pro Pro Pro Gly
    210                 215                 220

Val Gly Tyr Lys Asp Phe Arg Asp Pro Ser Thr Leu Trp Ser Gly Pro
225                 230                 235                 240

Asp Gly Glu Tyr Arg Met Val Met Gly Ser Lys His Asn Glu Thr Ile
                245                 250                 255

Gly Cys Ala Leu Ile Tyr His Thr Thr Asn Phe Thr His Phe Glu Leu
            260                 265                 270

Lys Glu Glu Val Leu His Ala Val Pro His Thr Gly Met Trp Glu Cys
        275                 280                 285

Val Asp Leu Tyr Pro Val Ser Thr Val His Thr Asn Gly Leu Asp Met
    290                 295                 300

Val Asp Asn Gly Pro Asn Val Lys Tyr Val Leu Lys Gln Ser Gly Asp
305                 310                 315                 320

Glu Asp Arg His Asp Trp Tyr Ala Ile Gly Ser Tyr Asp Ile Val Asn
                325                 330                 335

Asp Lys Trp Tyr Pro Asp Asp Pro Glu Asn Asp Val Gly Ile Gly Leu
            340                 345                 350

Arg Tyr Asp Phe Gly Lys Phe Tyr Ala Ser Lys Thr Phe Tyr Asp Gln
        355                 360                 365

His Lys Lys Arg Arg Val Leu Trp Gly Tyr Val Gly Glu Thr Asp Pro
    370                 375                 380

Gln Lys Tyr Asp Leu Ser Lys Gly Trp Ala Asn Ile Leu Asn Ile Pro
385                 390                 395                 400

Arg Thr Val Val Leu Asp Leu Glu Thr Lys Thr Asn Leu Ile Gln Trp
                405                 410                 415

Pro Ile Glu Glu Thr Glu Asn Leu Arg Ser Lys Lys Tyr Asp Glu Phe
            420                 425                 430

Lys Asp Val Glu Leu Arg Pro Gly Ala Leu Val Pro Leu Glu Ile Gly
        435                 440                 445

Thr Ala Thr Gln Leu Asp Ile Val Ala Thr Phe Glu Ile Asp Gln Lys
    450                 455                 460

Met Leu Glu Ser Thr Leu Glu Ala Asp Val Leu Phe Asn Cys Thr Thr
465                 470                 475                 480
```

-continued

```
Ser Glu Gly Ser Val Ala Arg Ser Val Leu Gly Pro Phe Gly Val Val
                485                 490                 495

Val Leu Ala Asp Ala Gln Arg Ser Glu Gln Leu Pro Val Tyr Phe Tyr
            500                 505                 510

Ile Ala Lys Asp Ile Asp Gly Thr Ser Arg Thr Tyr Phe Cys Ala Asp
        515                 520                 525

Glu Thr Arg Ser Ser Lys Asp Val Ser Val Gly Lys Trp Val Tyr Gly
    530                 535                 540

Ser Ser Val Pro Val Leu Pro Gly Glu Lys Tyr Asn Met Arg Leu Leu
545                 550                 555                 560

Val Asp His Ser Ile Val Glu Gly Phe Ala Gln Asn Gly Arg Thr Val
                565                 570                 575

Val Thr Ser Arg Val Tyr Pro Thr Lys Ala Ile Tyr Asn Ala Ala Lys
            580                 585                 590

Val Phe Leu Phe Asn Asn Ala Thr Gly Ile Ser Val Lys Ala Ser Ile
        595                 600                 605

Lys Ile Trp Lys Met Gly Glu Ala Glu Leu Asn Pro Phe Pro Leu Pro
    610                 615                 620

Gly Trp Thr Phe Glu Leu
625                 630


<210> SEQ ID NO 7
<211> LENGTH: 2003
<212> TYPE: DNA
<213> ORGANISM: Helianthus tuberosus

<400> SEQUENCE: 7

gggacgagta ccagtccagt cagtcaccat gcaaacccct gaaccctta cagaccttga      60

acatgaaccc cacacacccc tactggacca ccaccacaac ccaccaccac aaaccaccac    120

aaaacctttg ttcaccaggg ttgtgtccgg tgtcaccttt gttttattct tctttggttt    180

cgctatcgta ttcattgttc tcaaccaaca gaattcttct gttcgtatcg tcaccaattc    240

ggagaaatct tttataaggt attcgcagac cgatcgcttg tcgtgggaac ggaccgcttt    300

tcattttcag cctgccaaga attttattta cgatccagat ggtcagttgt ttcacatggg    360

ctggtaccat atgttctatc aatacaaccc atacgcaccg gtttggggca atatgtcatg    420

ggtcactca gtgtccaaag acatgatcaa ctggtacgag ctgccagtcg ctatggtccc     480

gaccgaatgg tatgatatcg agggcgtctt atccgggtct accacggtcc ttccaaacgg    540

tcagatcttt gcattgtata ctgggaacgc taatgatttt tcccaattac aatgcaaagc    600

tgtacccgta aacttatctg acccgcttct tattgagtgg gtcaagtatg aggataaccc    660

aatcctgtac actccaccag ggattgggtt aaaggactat cgggacccgt caacagtctg    720

gacaggtccc gatggaaagc ataggatgat catgggaact aaacgtggca atacaggcat    780

ggtacttgtt tactatacca ctgattacac gaactacgag ttgttggatg agccgttgca    840

ctctgttccc aacaccgata tgtgggaatg cgtcgacttt tacccggttt cgttaaccaa    900

tgatagtgca cttgatatgg cggcctatgg gtcgggtatc aaacacgtta ttaaagaaag    960

ttgggaggga catggaatgg attggtattc aatcgggaca tatgacgcga taaatgataa   1020

atggactccc gataacccgg aactagatgt cggtatcggg ttacggtgcg attacgggag   1080

gttttttgca tcaaagagtc tttatgaccc attgaagaaa aggaggatca cttggggtta   1140

tgttggagaa tcagatagtg ctgatcagga cctctctaga ggatgggcta ctgtttataa   1200

tgttggaaga acaattgtac tagatagaaa gaccgggacc catttacttc attggcccgt   1260
```

-continued

```
tgaggaagtc gagagtttga gatacaacgg tcaggagttt aaagagatca agctagagcc   1320

cggttcaatc attccactcg acataggcac ggctacacag ttggacatag ttgcaacatt   1380

tgaggtggat caagcagcgt tgaacgcgac aagtgaaacc gatgatattt atggttgcac   1440

cactagctta ggtgcagccc aaaggggaag tttgggacca tttggtcttg cggttctagc   1500

cgatggaacc ctttctgagt taactccggt ttatttctat atagctaaaa aggcagatgg   1560

aggtgtgtcg acacattttt gtaccgataa gctaaggtca tcactagatt atgatgggga   1620

gagagtggtg tatgggggca ctgttcctgt gttagatgat gaagaactca caatgaggct   1680

attggtggat cattcgatag tggaggggtt tgcgcaagga ggaaggacgg ttataacatc   1740

aagggcgtat ccaacaaaag cgatatacga acaagcgaag ctgttcttgt tcaacaacgc   1800

cacaggtacg agtgtgaaag catctctcaa gatttggcaa atggcttctg caccaattca   1860

tcaataccct ttttaattac cggctatcgc tatccttttt gttattggta tttatgtatc   1920

ttaattttct tttaaacctt tttatttgat aaatattagt tcttgttatt gtgcttctag   1980

taataaatga atggtgttat ggg                                          2003


<210> SEQ ID NO 8
<211> LENGTH: 615
<212> TYPE: PRT
<213> ORGANISM: Helianthus tuberosus

<400> SEQUENCE: 8

Met Gln Thr Pro Glu Pro Phe Thr Asp Leu Glu His Glu Pro His Thr
  1               5                  10                  15

Pro Leu Leu Asp His His His Asn Pro Pro Gln Thr Thr Thr Lys
             20                  25                  30

Pro Leu Phe Thr Arg Val Val Ser Gly Val Thr Phe Val Leu Phe Phe
         35                  40                  45

Phe Gly Phe Ala Ile Val Phe Ile Val Leu Asn Gln Gln Asn Ser Ser
     50                  55                  60

Val Arg Ile Val Thr Asn Ser Glu Lys Ser Phe Ile Arg Tyr Ser Gln
 65                  70                  75                  80

Thr Asp Arg Leu Ser Trp Glu Arg Thr Ala Phe His Phe Gln Pro Ala
                 85                  90                  95

Lys Asn Phe Ile Tyr Asp Pro Asp Gly Gln Leu Phe His Met Gly Trp
            100                 105                 110

Tyr His Met Phe Tyr Gln Tyr Asn Pro Tyr Ala Pro Val Trp Gly Asn
        115                 120                 125

Met Ser Trp Gly His Ser Val Ser Lys Asp Met Ile Asn Trp Tyr Glu
    130                 135                 140

Leu Pro Val Ala Met Val Pro Thr Glu Trp Tyr Asp Ile Glu Gly Val
145                 150                 155                 160

Leu Ser Gly Ser Thr Thr Val Leu Pro Asn Gly Gln Ile Phe Ala Leu
                165                 170                 175

Tyr Thr Gly Asn Ala Asn Asp Phe Ser Gln Leu Gln Cys Lys Ala Val
            180                 185                 190

Pro Val Asn Leu Ser Asp Pro Leu Leu Ile Glu Trp Val Lys Tyr Glu
        195                 200                 205

Asp Asn Pro Ile Leu Tyr Thr Pro Pro Gly Ile Gly Leu Lys Asp Tyr
    210                 215                 220

Arg Asp Pro Ser Thr Val Trp Thr Gly Pro Asp Gly Lys His Arg Met
225                 230                 235                 240
```

-continued

```
Ile Met Gly Thr Lys Arg Gly Asn Thr Gly Met Val Leu Val Tyr Tyr
                245                 250                 255

Thr Thr Asp Tyr Thr Asn Tyr Glu Leu Leu Asp Glu Pro Leu His Ser
            260                 265                 270

Val Pro Asn Thr Asp Met Trp Glu Cys Val Asp Phe Tyr Pro Val Ser
        275                 280                 285

Leu Thr Asn Asp Ser Ala Leu Asp Met Ala Ala Tyr Gly Ser Gly Ile
    290                 295                 300

Lys His Val Ile Lys Glu Ser Trp Glu Gly His Gly Met Asp Trp Tyr
305                 310                 315                 320

Ser Ile Gly Thr Tyr Asp Ala Ile Asn Asp Lys Trp Thr Pro Asp Asn
                325                 330                 335

Pro Glu Leu Asp Val Gly Ile Gly Leu Arg Cys Asp Tyr Gly Arg Phe
            340                 345                 350

Phe Ala Ser Lys Ser Leu Tyr Asp Pro Leu Lys Lys Arg Arg Ile Thr
        355                 360                 365

Trp Gly Tyr Val Gly Glu Ser Asp Ser Ala Asp Gln Asp Leu Ser Arg
    370                 375                 380

Gly Trp Ala Thr Val Tyr Asn Val Gly Arg Thr Ile Val Leu Asp Arg
385                 390                 395                 400

Lys Thr Gly Thr His Leu Leu His Trp Pro Val Glu Glu Val Glu Ser
                405                 410                 415

Leu Arg Tyr Asn Gly Gln Glu Phe Lys Glu Ile Lys Leu Glu Pro Gly
            420                 425                 430

Ser Ile Ile Pro Leu Asp Ile Gly Thr Ala Thr Gln Leu Asp Ile Val
        435                 440                 445

Ala Thr Phe Glu Val Asp Gln Ala Ala Leu Asn Ala Thr Ser Glu Thr
    450                 455                 460

Asp Asp Ile Tyr Gly Cys Thr Thr Ser Leu Gly Ala Ala Gln Arg Gly
465                 470                 475                 480

Ser Leu Gly Pro Phe Gly Leu Ala Val Leu Ala Asp Gly Thr Leu Ser
                485                 490                 495

Glu Leu Thr Pro Val Tyr Phe Tyr Ile Ala Lys Lys Ala Asp Gly Gly
            500                 505                 510

Val Ser Thr His Phe Cys Thr Asp Lys Leu Arg Ser Ser Leu Asp Tyr
        515                 520                 525

Asp Gly Glu Arg Val Val Tyr Gly Gly Thr Val Pro Val Leu Asp Asp
    530                 535                 540

Glu Glu Leu Thr Met Arg Leu Leu Val Asp His Ser Ile Val Glu Gly
545                 550                 555                 560

Phe Ala Gln Gly Gly Arg Thr Val Ile Thr Ser Arg Ala Tyr Pro Thr
                565                 570                 575

Lys Ala Ile Tyr Glu Gln Ala Lys Leu Phe Leu Phe Asn Asn Ala Thr
            580                 585                 590

Gly Thr Ser Val Lys Ala Ser Leu Lys Ile Trp Gln Met Ala Ser Ala
        595                 600                 605

Pro Ile His Gln Tyr Pro Phe
    610                 615
```